United States Patent
Damiano, Jr. et al.

(10) Patent No.: US 9,040,939 B2
(45) Date of Patent: May 26, 2015

(54) MEMBRANE SUPPORTS WITH REINFORCEMENT FEATURES

(75) Inventors: John Damiano, Jr., Apex, NC (US); Stephen E. Mick, Apex, NC (US); David P. Nackashi, Raleigh, NC (US)

(73) Assignee: PROTOCHIPS, INC., Raleigh, NC (US)

(*) Notice: Subject to any disclaimer, the term of this patent is extended or adjusted under 35 U.S.C. 154(b) by 231 days.

(21) Appl. No.: 12/529,429

(22) PCT Filed: Feb. 29, 2008

(86) PCT No.: PCT/US2008/055435
§ 371 (c)(1),
(2), (4) Date: Feb. 16, 2010

(87) PCT Pub. No.: WO2008/109406
PCT Pub. Date: Sep. 12, 2008

(65) Prior Publication Data
US 2010/0140497 A1   Jun. 10, 2010

Related U.S. Application Data

(60) Provisional application No. 60/892,677, filed on Mar. 2, 2007.

(51) Int. Cl.
*G21K 5/10* (2006.01)
*G02B 21/34* (2006.01)
*B01L 3/00* (2006.01)
(Continued)

(52) U.S. Cl.
CPC ............... *G02B 21/34* (2013.01); *B01L 3/508* (2013.01); *G01N 1/312* (2013.01); *G01N 1/36* (2013.01); *G01N 1/42* (2013.01); *H01J 37/20* (2013.01); *B01L 2300/0851* (2013.01); *H01J 2237/2003* (2013.01)

(58) Field of Classification Search
USPC .................................. 250/440.11; 269/289 R
See application file for complete search history.

(56) References Cited

U.S. PATENT DOCUMENTS 4,163,900 A * 8/1979 Warren et al. ............ 250/440.11
4,441,793 A * 4/1984 Elkins ............................ 359/398
(Continued)

FOREIGN PATENT DOCUMENTS

EP          0550173 A1    7/1993
JP          48047394 A    7/1973
(Continued)

OTHER PUBLICATIONS

Lindblom et al., Pulse Reverse Plating for Uniform Nickel Height in Zone Plates, Nov./Dec. 2006, Journal of Vacuum Science Technology.*

(Continued)

*Primary Examiner* — Nicole Ippolito
*Assistant Examiner* — Jason McCormack
(74) *Attorney, Agent, or Firm* — Tristan A. Fuierer; Moore & Van Allen, PLLC (57) ABSTRACT

A sample support structure with integrated support features and methods of making and using the reinforced membrane. The sample support structures are useful for supporting samples for analysis using microscopic techniques, such as electron microscopy, optical microscopy, x-ray microscopy, UV-VIS spectroscopy and nuclear magnetic resonance (NMR) techniques.

17 Claims, 4 Drawing Sheets

(51) Int. Cl.
*G01N 1/31* (2006.01)
*G01N 1/36* (2006.01)
*G01N 1/42* (2006.01)
*H01J 37/20* (2006.01)

(56) References Cited

U.S. PATENT DOCUMENTS

| | | | | |
|---|---|---|---|---|
| 4,672,797 | A | * | 6/1987 | Hagler ........................... 53/467 |
| 5,365,072 | A | | 11/1994 | Turner et al. |
| 6,140,652 | A | * | 10/2000 | Shlepr et al. ............. 250/440.11 |
| 6,972,417 | B2 | * | 12/2005 | Suganuma et al. ......... 250/492.1 |
| 6,989,542 | B2 | | 1/2006 | Moses et al. |
| 7,345,289 | B2 | * | 3/2008 | Iwasaki et al. ........... 250/440.11 |
| 7,745,802 | B2 | | 6/2010 | Nishiyama et al. |
| 7,923,700 | B2 | * | 4/2011 | Nishiyama ............... 250/440.11 |
| 2001/0050810 | A1 | * | 12/2001 | Lorincz ........................ 359/396 |
| 2002/0000524 | A1 | * | 1/2002 | Suzuki et al. ............ 250/492.21 |
| 2002/0166976 | A1 | * | 11/2002 | Sugaya et al. ............ 250/440.11 |
| 2006/0051251 | A1 | * | 3/2006 | Desrosiers et al. ............. 422/102 |
| 2006/0113476 | A1 | * | 6/2006 | Moore .......................... 250/311 |
| 2006/0243655 | A1 | * | 11/2006 | Striemer et al. ............. 210/490 |
| 2008/0250881 | A1 | * | 10/2008 | Dona ........................ 73/864.91 |
| 2008/0308731 | A1 | * | 12/2008 | Nishiyama et al. ............ 250/310 |

FOREIGN PATENT DOCUMENTS

| | | |
|---|---|---|
| JP | 03295440 | 12/1991 |
| JP | 04066839 A | 3/1992 |
| JP | 05251317 A | 2/1993 |
| JP | 06123800 A | 5/1994 |
| JP | 07333399 A | 12/1995 |
| JP | 08327511 | 12/1996 |
| JP | 09297093 | 11/1997 |
| JP | 10269978 A | 10/1998 |
| JP | 200174621 A | 3/2001 |
| JP | 2001351854 A | 12/2001 |
| JP | 2004515049 T | 5/2004 |
| JP | 2005216645 A | 8/2005 |
| JP | 200733336 A | 2/2007 |
| JP | 2007292702 A | 11/2007 |
| JP | 2008016249 A | 1/2008 |
| JP | 2008210765 A | 9/2008 |

OTHER PUBLICATIONS

Lindblom et al., Pulse Reverse Plating for Uniform Nickel Height in Zone Plates, 2006, Biomedical and X-ray Physics.*
Lindblom et al., Pulse Reverse Plating for Uniform Nickel Height in Zone Plates , Nov. 30, 2006.*
Lindblom et al., Pulse Reverse Plating for Uniform Nickel Height in Zone Plates, Nov. 30, 2006.*
International Searching Authority, International Search Report and Written Opinion, Jul. 31, 2008.
International Bureau, International Preliminary Report on Patentability, Sep. 8, 2009.
Koenig, Daniel R., et al., Drastic enhancement of nanoelectromechanical-system fabrication yield using electron-beam deposition, Applied Physics Letters, Jul. 5, 2004, pp. 157-159, vol. 85, No. 1.
Jefimovs, K., et al., Fabrication of Fresnel zone plates for hard X-rays, Microelectronic Engineering, 2007, pp. 1467-1470, vol. 84.
Lindblom, M., et al, Pulse reverse plating for uniform nickel height in zone plates, J. Vac. Sci. Technol. B, Nov./Dec., 2006, pp. 2848-2851, 24 (6).
Japanese Office Action, Jun. 28, 2012.
Supplementary European Search Report, Jan. 30, 2012.
European Office Action, Jan. 28, 2013.
Japanese Office Action, Feb. 25, 2014.

* cited by examiner

MEMBRANE SUPPORTS WITH REINFORCEMENT FEATURES

CROSS-REFERENCE TO RELATED APPLICATIONS

This application is filed under the provisions of 35 U.S.C. §371 and claims the priority of International Patent Application No. PCT/US08/55435 filed on 29 Feb. 2008 entitled "Membrane Supports with Reinforcement Features" in the name of John Damiano Jr., et al., which claims priority of U.S. Provisional Patent Application No. 60/892,677 filed on 2 Mar. 2007, both of which are hereby incorporated by reference herein in their entirety.

FIELD OF THE INVENTION

The invention relates to a reinforced membrane with integrated support features and methods of making and using the reinforced membrane.

BACKGROUND OF THE INVENTION

Very thin membranes are useful as sample supports for electron microscopy. Extremely thin membranes (<50 nm) are nearly electron transparent, and these supports are useful in several electron microscopy techniques, including SEM, TEM, and STEM, as well as optical microscopy, x-ray microscopy, UV-VIS spectroscopy and nuclear magnetic resonance (NMR). One concern that emerges for extremely thin membranes is strength; as the thickness of the membrane decreases, it is more likely to break during handling and burst if a differential pressure is applied across the membrane. Since certain microscopy techniques, such as the use of environmental cells, depend on sustaining differential pressure across a membrane, the strength of extremely thin membranes is of keen interest. It is well known that area of the membrane region impacts strength. For a given membrane thickness, a smaller-region membrane offers higher burst pressure—that is, a smaller region membrane can withstand greater pressure differential than a larger region membrane of the same thickness. In theory, one could continue shrinking the membrane region to extremely small dimensions to achieve a high burst pressure for a given membrane thickness, but a tiny membrane region would be difficult to use in situ, would restrict the sample size that could be imaged, and is generally not useful for microscopy or spectroscopy techniques.

The present invention discloses a novel reinforced thin membrane structure with integrated support features, and methods of fabrication for this structure. The structure provides a larger region membrane with support features that subdivide the large membrane into smaller regions. This structure offers the sample viewing region of a large, thin membrane with the strength of individual smaller membranes.

BRIEF DESCRIPTION OF THE INVENTION

The invention generally relates to a reinforced sample support structure.

In one aspect, the invention relates to a structure including an array of viewing regions supported by reinforcement regions.

In another aspect, the invention relates to a method of making a sample support structure, the method comprising the following steps which produces a sample support structure comprising an array of viewing regions supported by reinforcement regions: providing a substrate having a first surface and a second surface; depositing a first support layer on the first surface of the substrate; depositing a second support layer on the second surface of the substrate; removing a portion of the first support layer to expose the substrate; removing a portion of the substrate to yield a framing region; depositing a reinforcement layer on the second support layer; and removing a portion of the reinforcement layer to provide a viewing region comprising at least one viewing area and at least one reinforcement.

In still another aspect, the invention relates to a method of making a sample support structure, the method comprising the following steps which produces a sample support structure comprising an array of viewing regions supported by reinforcement regions: providing a substrate having a first surface and a second surface; depositing a first support layer on the first surface of the substrate; depositing a second support layer on the second surface of the substrate; depositing a reinforcement layer on the second support layer; removing a portion of the reinforcement layer to provide a viewing region comprising at least one viewing area and at least one reinforcement; removing a portion of the first support layer to expose the substrate; and removing a portion of the substrate to yield a framing region.

In yet another aspect, the invention relates to a method of making a sample support structure, the method comprising the following steps which produces a sample support structure comprising an array of viewing regions supported by reinforcement regions: providing a substrate having a first surface and a second surface; depositing a first support layer on the first surface of the substrate; depositing a second support layer on the second surface of the substrate; removing a portion of the first support layer to expose the substrate; removing a portion of the substrate to yield a framing region; and formation of support feature by thinning a region of the second support layer to provide one or more thinned viewing or imaging regions adjacent to one or more thicker reinforcement regions.

In another aspect, the invention relates to a method of making a sample support structure, the method comprising the following steps which produces a sample support structure comprising an array of viewing regions supported by reinforcement regions: providing a substrate having a first surface and a second surface; depositing a first support layer on the first surface of the substrate; depositing a second support layer on the second surface of the substrate; formation of support feature by thinning a region of the second support layer to provide one or more thinned viewing or imaging regions adjacent to one or more thicker reinforcement regions; removing a portion of the first support layer to expose the substrate; and removing a portion of the substrate to yield a framing region.

Other aspects, features and advantages of the invention will be more fully apparent from the ensuing disclosure and appended claims.

DETAILED DESCRIPTION OF THE INVENTION

The present invention relates to sample support structures, methods of making sample support structures, and methods of using sample support structures. The sample support structures are useful for supporting samples for analysis using microscopic techniques, such as electron microscopy, optical microscopy, x-ray microscopy, UV-VIS spectroscopy and nuclear magnetic resonance (NMR) techniques.

As defined herein, "semiconductor" means a material, such as silicon, that is intermediate in electrical conductivity between conductors and insulators.

As defined herein, "photolithography" means a process, which uses beams of light, projected through a reticle, to pattern or etch a photosensitive material.

When a given component such as a layer, region or substrate is referred to herein as being disposed or formed "on" another component, that given component can be directly on the other component or, alternatively, intervening components (for example, one or more coatings, layers, interlayers) can also be present. It will be further understood that the term "layered on" is used to describe how a given component is positioned or situated in relation to another component. Hence, the term "layered on" is not intended to introduce any limitations relating to particular methods of material transport, deposition, or fabrication. When a sample is described as being "on" a structure, such as a sample platform, such sample could be either in direct contact with the structure, or could be in contact with one or more layers or films that are interposed between the sample and structure.

As defined herein, an environmental cell is a sealed device placed within the TEM. The environmental cell sustains a wet and/or atmospheric pressure environment inside the cell, while the surrounding TEM chamber is held under high vacuum. Typically, a thin membrane is used as a vacuum window for the environmental cell.

As defined herein, an "array" corresponds to a structure having at least one viewing/membrane region supported by and divided by at least one reinforcement region. As disclosed herein, the at least one reinforcement region may be arranged to frame a square viewing/membrane region. Alternatively, it is to be appreciated by one skilled in the art that the reinforcement region may be arranged to frame a rectangular, circular, elliptical, or polygonal viewing/membrane region. Moreover, each reinforcement region may be equally or non-equally sized such that the framed viewing/membrane region are equally or non-equally sized, respectively.

Figure 1:
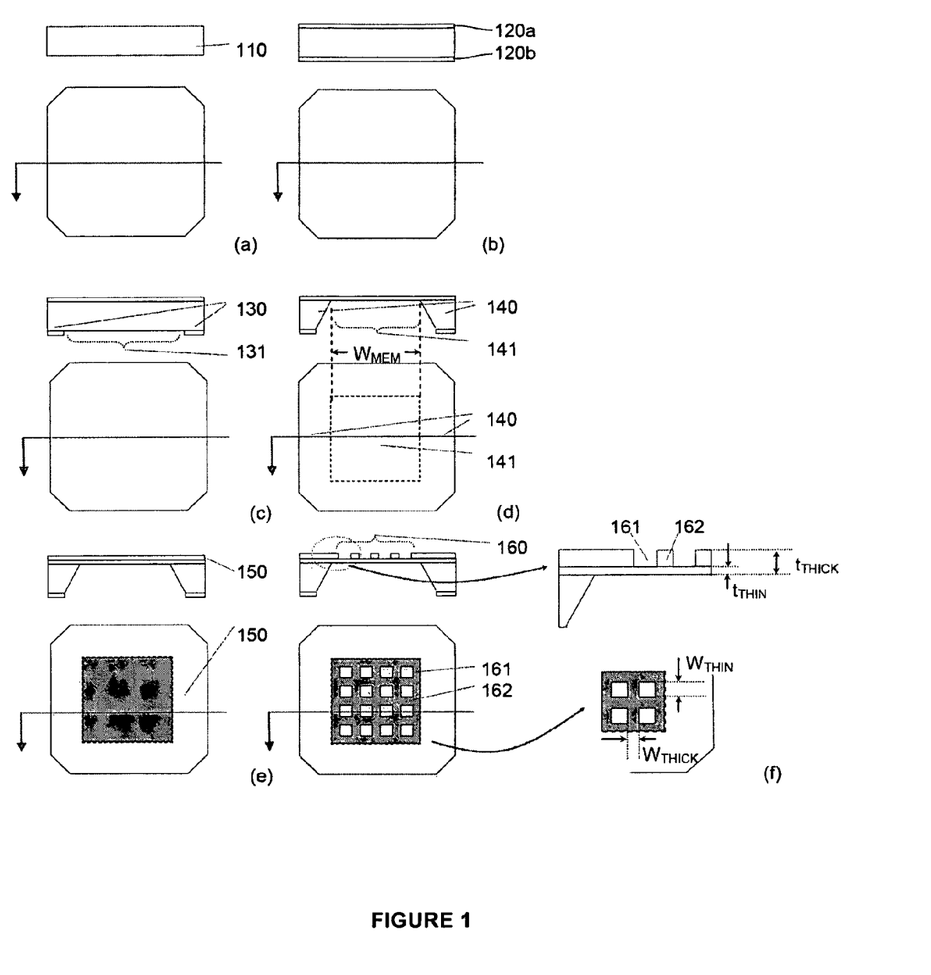
FIG. 1 illustrates an embodiment in which the frame is formed first, followed by formation and patterning of a reinforcement layer.
Figure 2:
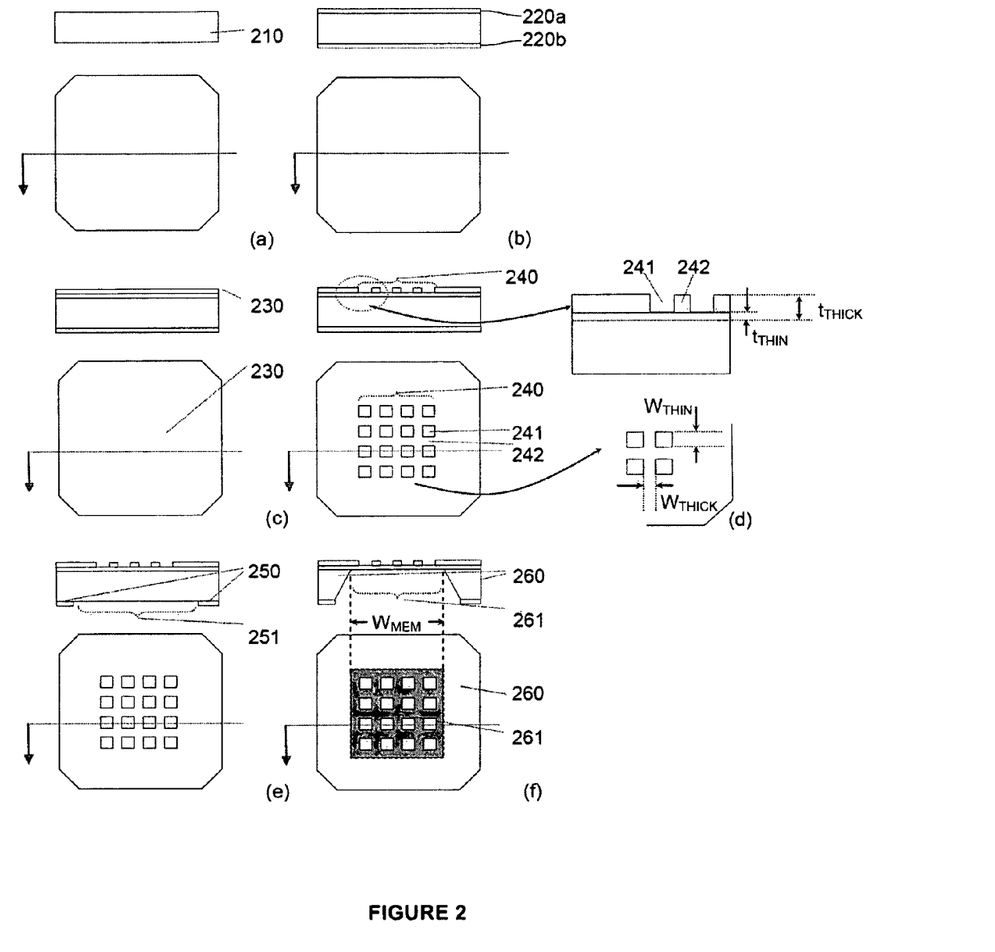
FIG. 2 illustrates an embodiment in which the reinforcement layer is formed first, followed by formation and patterning of the frame.

In one aspect, the present invention relates to depositing and patterning a reinforcement layer onto the support layer surface. Examples of this aspect are illustrated in FIGS. 1 and 2. The reinforcement layer provides additional mechanical strength to the membrane. Openings in the reinforcement layer provide access to viewing/imaging regions of the support layer. The pattern of openings in, the thickness of, and/or the composition of the supporting layer can be varied to satisfy requirements for specific applications and optimize performance.

FIG. 1 shows an embodiment in which the frame is formed first, followed by formation and patterning of a reinforcement layer. This aspect of the invention provides a method generally including one or more of the following steps illustrated in FIG. 1:
(a) Providing a substrate 110;
(b) Depositing sample support layers 120a, 120b on the substrate 110;
(c) Removing a portion 131 of the sample support layer 120b to expose the substrate 110;
(d) Removing a portion 141 of the substrate 110 to yield a framing region 140;
(e) Depositing a reinforcement layer 150 on the sample support layer 120a; and
(f) Removing a portion of the reinforcement layer 150 to provide a viewing or imaging region 160, with at least one viewing area 161 and at least one reinforcement 162.

Referring to FIG. 1(a) a substrate 110 is provided. The substrate 110 may, for example, be composed of a silicon material, such as monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, or other conducting, semiconducting, or insulating materials, as well as other materials known to one of skill in the art, and combinations thereof. Semiconductor materials may be doped to improve conductivity. In some embodiments, the substrate 110 may have a thickness ranging from about 2 to about 1000 μm, preferably from about 100 to about 750 μm, and most preferably about 250 μm to about 350 μm.

Referring to FIG. 1(b), sample support layers 120a and 120b are deposited on the substrate 110. For example, in one embodiment, the sample support layers 120a and 120b are deposited on frontside and backside surfaces of the substrate 110. The material for sample support layers 120a, 120b is preferably selected to provide a stress in the sample support layers 120a, 120b that is low and tensile. Examples of suitable materials for the sample support layers 120a, 120b include monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, or other conducting, semiconducting, or insulating materials, as well as other materials known to one of skill in the art, and combinations thereof. In some embodiments, the sample support layers 120a, 120b are deposited to a thickness ranging from about 1 to about 5000000 nm, preferably from about 25 to about 1000 nm, most preferably from about 50 to about 200 nm. While the description here focuses on the embodiment in which 120a and 120b are made from the same material and the same thickness, in alternative embodiments, these layers may be made from different materials and/or have different thicknesses. In addition, it should be appreciated that the substrate 110 and the sample support layers 120a, 120b may be the same materials or different materials. For example, the substrate may be a silicon material and the sample support layers may be silicon nitride.

Referring to FIG. 1(c), the sample support layer 120b is modified to remove one or more portions and leave one or more other portions. As illustrated, in some embodiments, a central portion 131 may be substantially or completely removed, leaving a framing region 130. In some cases, removal may be achieved by patterning and etching, e.g., using photolithography followed by wet chemical etching and/or reactive ion etching to remove a portion of the sample support layer 120b. The etchant selected depends on the materials used, but it is preferably capable of etching sample support layer 120b without significantly etching the underlying substrate 110. The etched sample support layer 120b includes one or more regions 130 with sample support layer 120b and one or more etched regions 131 where sample support layer 120b has been substantially or completely removed. In regions 131 lacking sample support layer 120b, the underlying substrate 110 is exposed. In one embodiment, a single region 131 substantially lacking sample support layer 120b is fully surrounded by a region 130 with sample support layer 120b, thereby providing a framing region that runs substantially along an outer edge of the sample support structure. It should be appreciated by one skilled in the art that the framing region that runs substantially along an outer edge of the sample support structure may be square, rectangular, circular, elliptical or polygonal as well as symmetrical or unsymmetrical. In other words, the "frame" may have a substantially similar width all the way around the sample support structure or the width may vary depending on the end needs of the sample support structure.

Referring to FIG. 1(d), a portion of the substrate 110 is removed, e.g., by etching. Etching may, for example, involve the use of wet chemical etching and/or reactive ion etching in regions 131 without sample support layer 120b. The etch process may selected such that it selectively etches substrate 110 without also significantly etching sample support layers 120a or 120b. Etching continues until the substrate 110 is substantially or completely removed in regions 141 without sample support layer 120b, yielding a frame region 140 where the substrate 110 is retained, and a membrane region 141, where the substrate 110 is substantially or completely removed.

Referring to FIG. 1(e), a reinforcement layer 150 is deposited on sample support layer 120a. In some embodiments, the reinforcement layer 150 is deposited to a thickness ranging from about 1 to about 1000000 nm, more preferably from about 50 to about 50000 nm, most preferably from about 200 to about 5000 nm. Examples of suitable materials for the reinforcement layer 150 include metals, semiconductors and/or insulators, such as monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, or other conducting, semiconducting, or insulating materials, as well as other materials known to one of skill in the art, and combinations thereof. In one embodiment, the reinforcement layer may be electrically charged. For example, if the reinforcement layer were a metal and the sample support layer is silicon nitride, a voltage may be applied to the reinforcement layer which may be useful during electron microscopy applications. It should be appreciated that the material of the reinforcement layer may be the same as or different from the material of the sample support layer 120a. For example, the sample support layer may be silicon nitride and the reinforcement layer may be a metal.

Referring to FIG. 1(f), one or more portions of reinforcement layer 150 are completely or substantially removed to yield reinforced regions with and without the reinforcement layer. Reinforcement layer may, for example, be patterned and etched, e.g., using photolithography followed by wet chemical etching and/or reactive ion etching. One or more regions of the reinforcement layer 150 are removed, forming a reinforced region 160. Reinforced region 160 includes membrane regions 161 without reinforcement layer 150 and reinforcement regions 162 with reinforcement layer 150. Membrane regions 161 without reinforcement layer 150 have film thickness $t_{THIN}$ (e.g., approximately equal to the thickness of sample support layer 120a). These regions retain the desirable characteristics of a standard thin membrane support. Reinforcement regions 162 with reinforcement layer 150 have thickness $t_{THICK}$ (e.g., approximately equal to the sum of sample support layer 120a and reinforcement layer 150). These regions divide and define the reinforced region 160 into one or more smaller membrane regions.

FIG. 2 shows another embodiment of this aspect of the invention whereby the reinforcement layer is formed first, followed by formation and patterning of the frame. This aspect of the invention provides a method generally including one or more of the following steps:
 (a) Providing a substrate 210
 (b) Depositing sample support layers 220a, 220b on the substrate
 (c) Depositing a reinforcement layer 230 on the sample support layer 220a
 (d) Removing a portion of the reinforcement layer 230 to provide a viewing or imaging region 240, with viewing areas 241 and reinforcements 242
 (e) Removing a portion 251 of the sample support layer 220b to expose the substrate 210
 (f) Removing a portion 261 of the substrate 210 to yield a frame 260.

Referring to FIG. 2(a) a substrate 210 is provided. The substrate 210 may, for example, be composed of a silicon material, such as monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, or other conducting, semiconducting, or insulating materials, as well as other materials known to one of skill in the art, and combinations thereof. Semiconductor materials may be doped to improve conductivity. In some embodiments, the substrate 210 may have a thickness ranging from about 2 to about 1000 μm, preferably from about 100 to about 750 μm, most preferably from about 250 μm to about 350 μm.

Referring to FIG. 2(b), sample support layers 220a, 220b are deposited on the substrate 210. For example, in one embodiment, the sample support layers 220a, 220b are deposited on the frontside and backside surfaces of substrate 210. The material for sample support layers 220a, 220b is preferably selected to provide a stress in the sample support layers 220a, 220b that is low and tensile. Examples of suitable materials for the sample support layers 220a,220b include monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, or other conducting, semiconducting, or insulating materials, as well as other materials known to one of skill in the art, and combinations thereof. In some embodiments, the sample support layers 220a, 220b are deposited to a thickness ranging from about 100 to about 5000000 nm, preferably from about 25 to about 1000 nm, most preferably from about 50 to about 200 nm. While the description here focuses on the embodiment in which 220a and 220b are made from the same material and the same thickness, in alternative embodiments, these layers may be made from different materials and/or different thicknesses. In addition, it should be appreciated that the substrate 210 and the sample support layers 220a, 220b may be the same materials or different materials. For example, the substrate may be a silicon material and the sample support layers may be silicon nitride.

Referring to FIG. 2(c), a reinforcement layer 230 is deposited on sample support layer 220a. In some embodiments, the reinforcement layer 230 is deposited to a thickness ranging from about 1 to about 1000000 nm, more preferably from about 50 to about 50000 nm, most preferably from about 200 to about 5000 nm. Examples of suitable materials for the reinforcement layer 230 include monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, or other conducting, semiconducting, or insulating materials, as well as other materials known to one of skill in the art, and combinations thereof. In one embodiment, the reinforcement layer may be electrically charged. For example, if the reinforcement layer were a metal and the sample support layer is silicon nitride, a voltage may be applied to the reinforcement layer which may be useful during electron microscopy applications. It should be appreciated that the material of the reinforcement layer may be the same as or different from the material of the sample support layer 220a.

Referring to FIG. 2(d), one or more portions 241 of reinforcement layer 230 are completely or substantially removed to yield reinforced regions with 242 and without 241 the reinforcement layer 230. Reinforcement layer 230 may, for example, be patterned and etched, e.g., using photolithography followed by wet chemical etching and/or reactive ion etching. One or more regions of the reinforcement layer 230 are removed, forming a reinforced region 240. Reinforced region 240 includes membrane regions 241 without reinforcement layer 230 and reinforcement regions 242 with reinforcement layer 230.

Referring to FIG. 2(e), the sample support layer 220b is modified to remove one or more portions and leave one or more other portions. As illustrated, in some embodiments, a central portion 251 may be substantially or completely removed, leaving a framing region 250. In some cases, removal may be achieved by patterning and etching, e.g., using photolithography followed by wet chemical etching and/or reactive ion etching to remove a portion of the sample support layer 220b. The etchant selected depends on the materials used, but it is preferably capable of etching sample support layer 220b without significantly etching the underlying substrate 210. The etched sample support layer 220b includes one or more regions 250 with sample support layer 220b and one or more etched regions 251 where sample support layer 220b has been substantially or completely removed. In regions 251 lacking sample support layer 220b, the underlying substrate 210 is exposed. In one embodiment, a single region 251 substantially lacking sample support layer 220b is fully surrounded by a region 250 with sample support layer 220b, thereby providing a framing region that runs substantially along an outer edge of the sample support structure. It should be appreciated by one skilled in the art that the framing region that runs substantially along an outer edge of the sample support structure may be square, rectangular, circular, elliptical or polygonal as well as symmetrical or unsymmetrical. In other words, the "frame" may have a substantially similar width all the way around the sample support structure or the width may vary depending on the end needs of the sample support structure.

Referring to FIG. 2(f), a portion of the substrate 210 is removed, e.g., by etching. Etching may, for example, involve the use of wet chemical etching and/or reactive ion etching in regions 251 without sample support layer 220b. The etch process may be selected such that it selectively etches substrate 210 without also significantly etching sample support layers 220a, 220b. Etching continues until the substrate 210 is substantially or completely removed in regions 261 without sample support layer 220b, yielding a frame region 260 where the substrate 210 is retained, and a membrane region 261, where the substrate 210 is substantially or completely removed. Membrane regions 241 without reinforcement layer 230 may in some embodiments have film thickness $t_{THIN}$ (e.g., approximately equal to the thickness of sample support layer 220a). These regions retain the desirable characteristics of a standard thin membrane support. Reinforcement regions 242 with reinforcement layer 230 have thickness $t_{THICK}$ (e.g., approximately equal to the sum of sample support layer 220a and reinforcement layer 230). These regions divide and define the reinforced region 240 into one or more smaller membrane regions.

Figure 3:
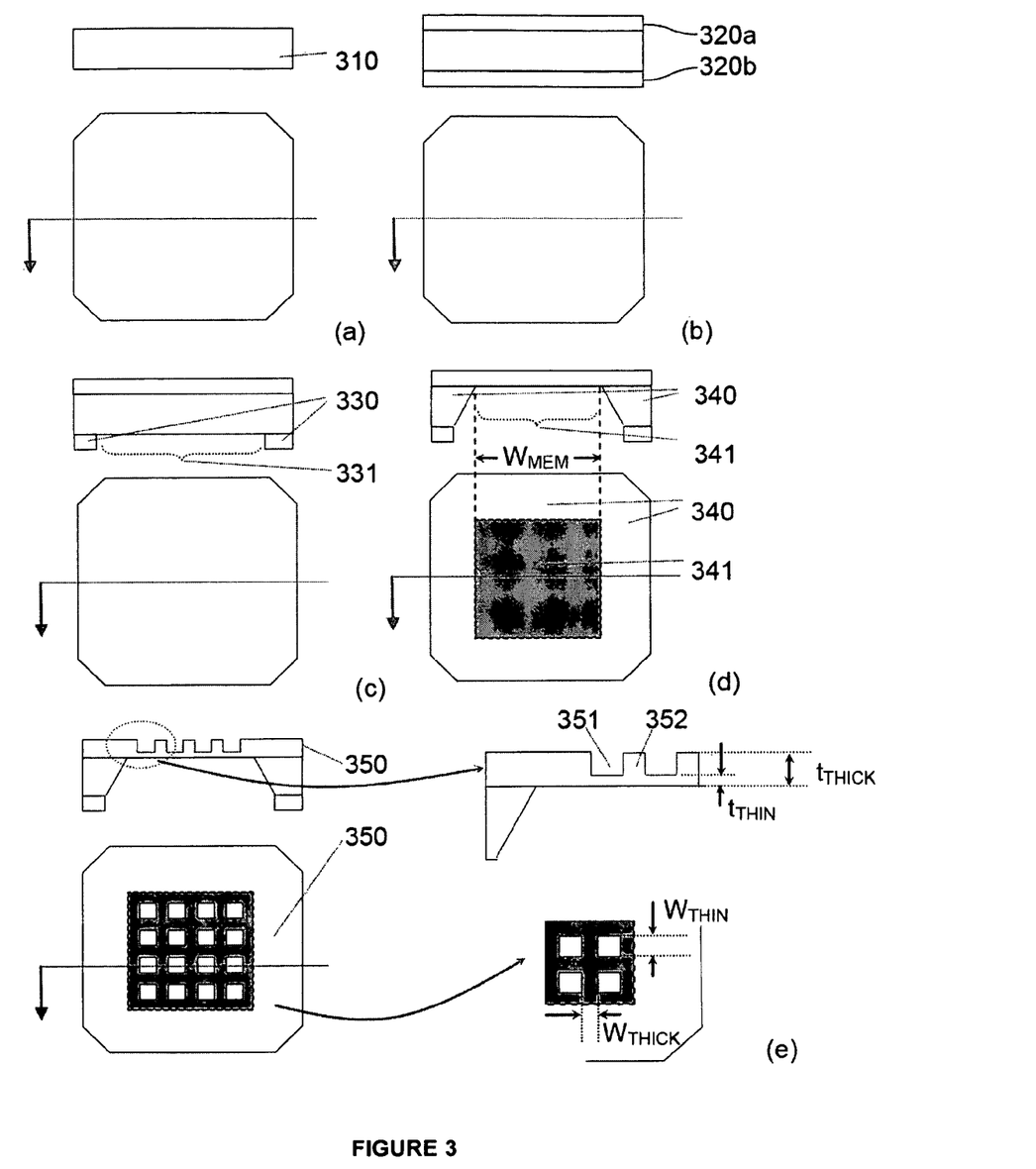
FIG. 3 illustrates an embodiment in which the frame is formed first, followed by formation of the reinforced platform.
Figure 4:
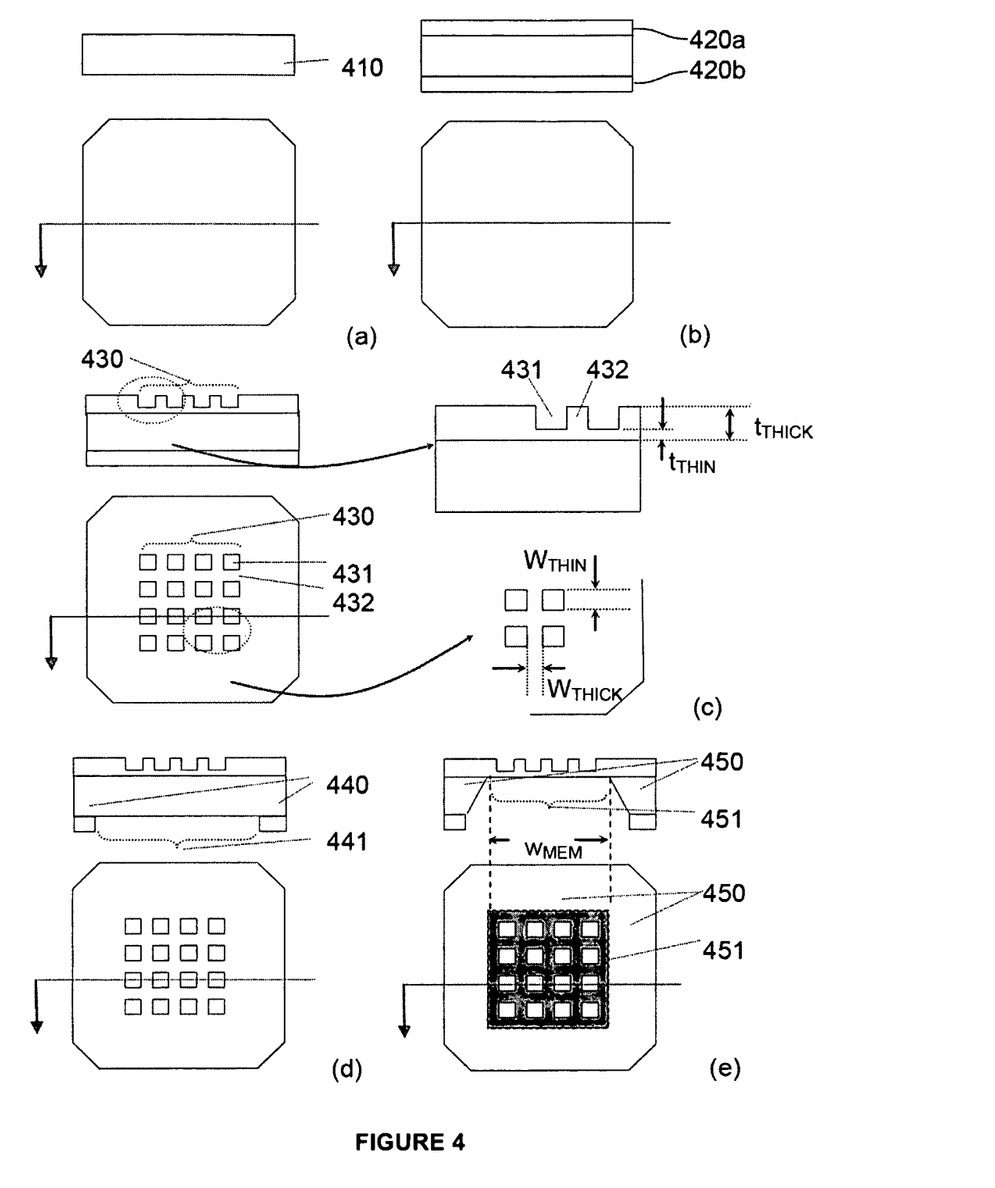
FIG. 4 illustrates an embodiment in which the reinforced platform is formed first, followed by formation of the frame.

Another aspect of the invention involves a sample support structure having integrated or monolithic membrane support features. Examples of this aspect are illustrated in FIGS. 3 and 4. The reinforcement region provides additional mechanical strength to the viewing area. The pattern, thickness, and/or composition of the supporting regions can be varied to satisfy requirements for specific applications and optimize performance.

In general, this aspect starts with a membrane layer of $t_{THICK}$. Regions of the membrane are thinned to a thickness $t_{THIN}$ to provide viewing regions for sample imaging, while the thick portions provide mechanical strength. One advantage of this approach is that the supporting features are of the same material composition as the viewing regions, so temperature variations will not induce additional stress on the membrane due to coefficient of thermal expansion (CTE) mismatch. Use of an identical material in the thick/thin regions also avoids introducing extra peaks during material analysis. The ensuing sections provide examples of processes for manufacturing such sample support structures. In each of the ensuing examples, the deposition processes may, for example, employ PVD, LPCVD, MOCVD, ALD, or electroplating/electrodeposition, or a combination of these. Etch processes may, for example, employ wet etching, reactive ion etching, sputtering, ion milling, or a combination of these.

In a particularly preferred embodiment, the substrate includes silicon, the sample support layers include silicon nitride and the reinforcement layer includes metal.

FIG. 3 shows an embodiment in which the frame is formed first, followed by formation of the reinforced platform. This embodiment of the invention provides a method generally including one or more of the following steps:

(a) Providing a substrate 310
(b) Depositing sample support layers 320a, 320b on the substrate 310
(c) Removing a portion 331 of the sample support layer 320b to expose the substrate 310
(d) Removing a portion 341 of the substrate 310 to yield a frame 340
(e) Formation of support features, e.g., by removing a portion of the sample support layers 320a to provide one or more thinned viewing or imaging regions 351 adjacent to a thicker reinforcement region 352.

Referring to FIG. 3(a) a substrate 310 is provided. The substrate 310 may, for example, be composed of a silicon material, such as monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, or other conducting, semiconducting, or insulating materials, as well as other materials known to one of skill in the art, and combinations thereof. Semiconductor materials may be doped to improve conductivity. In some embodiments, the substrate 310 may have a thickness ranging from about 2 to about 1000 µm, preferably from about 100 to about 750 µm, most preferably from about 250 µm to about 350 µm.

Referring to FIG. 3(b), sample support layers 320a, 320b are deposited on the substrate 310. For example, in one embodiment, the sample support layers 320a, 320b are deposited on the frontside and backside surfaces of substrate 310. The material for sample support layers 320a, 320b is preferably selected to provide a stress in the sample support layers 320a, 320b that is low and tensile. Examples of suitable materials for the sample support layers 320a, 320b include monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, or other conducting, semiconducting, or insulating materials, as well as other materials known to one of skill in the art, and combinations thereof. In some embodiments, the sample support layers 320a, 320b are deposited to a thickness ranging from about 100 to about 5000000 nm, preferably from about 25 to about 1000 nm, most preferably from about 50 to about 200 nm. While the description here focuses on the embodiment in which 320a and 320b are made from the same material and the same thickness, in alternative embodiments, these layers may be made from different materials and/or different thicknesses. In addition, it should be appreciated that the substrate 310 and the sample support layers 320a, 320b may be the same materials or different materials. For example, the substrate may be a silicon material and the sample support layers may be silicon nitride.

Referring to FIG. 3(c), the sample support layer 320b is modified to remove one or more portions 331 and leave one or more other portions 330. As illustrated, in some embodiments, a central portion 331 may be substantially or completely removed, leaving a framing region 330. In some cases, removal may be achieved by patterning and etching, e.g., using photolithography followed by wet chemical etching and/or reactive ion etching to remove a portion of the sample support layer 320b. The etchant selected depends on the materials used, but it is preferably capable of etching sample support layer 320b without significantly etching the underlying substrate 310. The etched sample support layer 320b includes one or more regions 330 with sample support layer 320b and one or more etched regions 331 where sample support layer 320b has been substantially removed. In regions 331 lacking sample support layer 320b, the underlying substrate 310 is exposed. In one embodiment, a single region 331 substantially lacking sample support layer 320b is fully surrounded by a region 330 with sample support layer 320b, thereby providing a framing region that runs substantially along an outer edge of the sample support structure. It should be appreciated by one skilled in the art that the framing region that runs substantially along an outer edge of the sample support structure may be square, rectangular, circular, elliptical or polygonal as well as symmetrical or unsymmetrical. In other words, the "frame" may have a substantially similar width all the way around the sample support structure or the width may vary depending on the end needs of the sample support structure.

Referring to FIG. 3(d), a portion of the substrate 310 is removed, e.g., by etching. Etching may, for example, involve the use of wet chemical etching and/or reactive ion etching in regions 331 without sample support layer 320b. The etch process may selected such that it selectively etches substrate 310 without also significantly etching sample support layers 320a, 320b. Etching continues until the substrate 310 is substantially or completely removed in regions 341 without sample support layer 320b, yielding a frame region 340 where the substrate 310 is retained, and a membrane region 341, where the substrate 310 is substantially or completely removed.

Support features are formed in the sample support layer 320a. For example, sample support layer 320a may be etched down to a thickness $t_{THIN}$, e.g., using photolithography followed by wet chemical etching and/or reactive ion etching. As shown in FIG. 3(e), portions of the sample support layer 320a are removed to provide a reinforced platform 350. The sample support layer 320 is preferably not thinned in the frame region 340. In the reinforced region 350, there are two distinct regions: regions with as-deposited film thickness $t_{THICK}$ 352 and regions that have been thinned to $t_{THIN}$ 351. The regions that have been thinned to $t_{THIN}$ 351 may have the characteristics of a standard thin membrane, while regions with as-deposited film thickness $t_{THICK}$ 352, with width $W_{THICK}$, subdivide the larger membrane region 341 into smaller membrane regions. These smaller membrane regions, with width $W_{THIN}$ may provide higher burst strength than larger membranes with the same membrane thickness, while the large number of smaller membrane regions, taken as a whole, offer a large viewable region. This technique also pulls the edge of the thin membranes away from the edge of the frame region 340 around the perimeter of the larger membrane region 341. Since the interface between large membrane region 341 and frame region 340 is often the site of failure during membrane burst pressure testing, use of a thicker membrane 352 rather than a thinner membrane 351 at this interface will provide a strengthened membrane region 341.

FIG. 4 shows another embodiment in which the reinforced platform is formed first, followed by formation of the frame. This aspect of the invention provides a method generally including one or more of the following steps:
  (a) Providing a substrate 410
  (b) Depositing sample support layers 420a, 420b on the substrate 410
  (c) Formation of support features, e.g., by removing a portion of the sample support layers 420a to provide one or more thinned viewing or imaging regions 431 adjacent to a thicker reinforcement region 432
  (d) Removing a portion 441 of the sample support layer 420b to expose the substrate 410
  (e) Removing a portion 451 of the substrate 410 to yield a frame 450.

Referring to FIG. 4(a) a substrate 410 is provided. The substrate 410 may, for example, be composed of a silicon material, such as monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, or other conducting, semiconducting, or insulating materials, as well as other materials known to one of skill in the art, and combinations thereof. Semiconductor materials may be doped to improve conductivity. In some embodiments, the substrate 410 may have a thickness ranging from about 2 to about 1000 µm, preferably from about 100 to about 750 µm, most preferably from about 250 µm to about 350 µm.

Referring to FIG. 4(b), sample support layers 420a, 420b are deposited on the substrate 410. For example, in one embodiment, the sample support layers 420a, 420b are deposited frontside and backside surfaces of substrate 410. The material for sample support layers 420a, 420b is preferably selected to provide a stress in the sample support layers 420a, 420b that is low and tensile. Examples of suitable materials for the sample support layers 420a, 420b include monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, or other conducting, semiconducting, or insulating materials, as well as other materials known to one of skill in the art, and combinations thereof. In some embodiments, the sample support layers 420a, 420b are deposited to a thickness ranging from about 100 to about 5000000 nm, preferably from about 25 to about 1000 nm, most preferably from about 50 to about 200 nm. While the description here focuses on the embodiment in which 420a and 420b are made from the same material and the same thickness, in alternative embodiments, these layers may be made from different materials and/or different thicknesses. In addition, it should be appreciated that the substrate 410 and the sample support layers 420a, 420b may be the same materials or different materials. For example, the substrate may be a silicon material and the sample support layers may be silicon nitride.

Support features are formed in the sample support layer 420a. For example, sample support layer 420a may be etched down to a thickness $t_{THIN}$, e.g., using photolithography followed by wet chemical etching and/or reactive ion etching. As shown in FIG. 4(c), portions of the sample support layer 420a are removed to provide a reinforced membrane region 430. The sample support layer 420a is preferably not thinned in the frame region 450. In the reinforced region 430, there are two distinct regions: regions with as-deposited film thickness $t_{THICK}$ 432 and regions that have been thinned to $t_{THIN}$ 431. The regions that have been thinned to $t_{THIN}$ 431 may have the characteristics of a standard thin membrane, while regions with as-deposited film thickness $t_{THICK}$ 432, with width $W_{THICK}$, subdivide the larger membrane region 451 into smaller membrane regions. These smaller membrane regions, with width $W_{THIN}$ may provide higher burst strength than larger membranes with the same membrane thickness, while the large number of smaller membrane regions, taken as a whole, offer a large viewable region. This technique also pulls the edge of the thin membranes away from the edge of the frame region 450 around the perimeter of the larger membrane region 451. Since the interface between large membrane region 451 and frame region 450 is often the site of failure during membrane burst pressure testing, use of a thicker membrane 432 rather than a thinner membrane 431 at this interface will provide a strengthened membrane region 451.

Referring to FIG. 4(c), the sample support layer 420b is modified to remove one or more portions 431 and leave one or more other portions 432. As illustrated, in some embodiments, a central portion 431 may be substantially or completely removed, leaving a framing region 432. In some cases, removal may be achieved by patterning and etching, e.g., using photolithography followed by wet chemical etching and/or reactive ion etching to remove a portion of the sample support layer 420b. The etchant selected depends on the materials used, but it is preferably capable of etching sample support layer 420b without significantly etching the underlying substrate 410. The etched sample support layer 420b includes one or more regions 430 with sample support layer 420b and one or more etched regions 431 where sample support layer 420b has been substantially or completely removed. In regions 431 lacking sample support layer 420b, the underlying substrate 410 is exposed. In one embodiment, a single region 451 substantially lacking sample support layer 420b is fully surrounded by a region 450 with sample support layer 420b, thereby providing a framing region that runs substantially along an outer edge of the sample support structure. It should be appreciated by one skilled in the art that the framing region that runs substantially along an outer edge of the sample support structure may be square, rectangular, circular, elliptical or polygonal as well as symmetrical or unsymmetrical. In other words, the "frame" may have a substantially similar width all the way around the sample support structure or the width may vary depending on the end needs of the sample support structure.

Referring to FIG. 4(d), a portion of the substrate 410 is removed, e.g., by etching. Etching may, for example, involve the use of wet chemical etching and/or reactive ion etching in regions 441 without sample support layer 420b. The etch process may be selected such that it selectively etches substrate 410 without also significantly etching sample support layers 420a, 420b. Etching continues until the substrate 410 is substantially or completely removed in regions 441 without sample support layer 420b, yielding a frame region 440 where the substrate 410 is retained, and a membrane region 441, where the substrate 410 is substantially or completely removed.

In a particularly preferred embodiment, the substrate includes silicon and the sample support layer which is then patterned/etched to create thinned regions for observation includes silicon nitride.

The sample support structure of the invention may be useful in a variety of settings. Examples include electron and/or ion beam analysis, electron microscopy techniques, such as transmission electron microscopy. The sample support structures of the present invention have a number of improved properties, as compared to support structures of the art. For example, samples analyzed using the sample support structures of the present invention exhibit decreased drift, as compared to samples analyzed using sample support structures of the art. In addition, the presently described structures have increased rigidity; may in some embodiments lack the presence of grids, etc. which are required for structures of the art, and which result in lower quality imaging; and the sample support structures of the present invention may be used at various temperatures, ranging from very low to very high. Furthermore, the sample support structures of the present invention may have consistent thickness and low stress.

The sample support of the invention is, in some embodiments, highly resistant to temperature changes. Consequently, in certain uses of the sample support structure, the sample support structure may be heated or cooled during processing.

The sample support structure may be useful for supporting samples containing a variety of components. In a particular non-limiting embodiment, various components that may be supported by the sample support structure include biological materials, whole cells, sections of cells, eukaryotic cells, prokaryotic cells, chemicals, proteins, peptides, polymers, nucleic acids, small molecules, and various combinations of these types of materials. In an embodiment, a protein sample may be supported by the sample support structure. In one embodiment, a protein and a compound, or a ligand, which interacts with the protein may be supported by the sample support structure.

Further, the sample support structures may be useful in tomography studies, in which the sample support structure is tilted to obtain a series of images from different angles.

Non-limiting uses of the sample support structures include use in: transmission electron microscopy (TEM) scanning electron microscopy (SEM), scanning transmission electron microscopy (STEM), and scanning tunneling microscopy (STM). The use of the sample support structures in other applications known to one of skill in the art are contemplated herein.

Samples to be analyzed by the above techniques may be prepared in a number of ways, such as: cryofixation, fixation, dehydration, embedding, sectioning, staining, freeze-fracture or freeze-etch, ion beam milling, conductive coating, and/or, in scanning electron microscopy, evaporation, thin-film deposition, or sputtering of carbon, gold, gold/palladium, platinum or other conductive material to avoid charging of non conductive specimens in a scanning electron microscope.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

We claim:

1. A reinforced sample support structure comprising (a) an array comprising more than one viewing region, wherein the viewing regions are supported by and divided by reinforcement regions, and the reinforcement regions and the viewing regions consist of the same material, the reinforcement regions are thicker than the viewing regions, and the viewing regions are electron transparent, and (b) a framing region surrounding the array, wherein the framing region runs substantially along an outer edge of the reinforced sample support structure, wherein the reinforcement regions are positioned above the viewing regions and the framing region is positioned below the viewing regions.

2. The reinforced sample support structure of claim 1 wherein the viewing regions and the reinforcement regions consist of material selected from the group consisting of monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, and combinations thereof.

3. The reinforced sample support structure of claim 1 wherein the viewing regions and reinforcement regions consist of silicon nitride.

4. The reinforced sample support structure of claim 1, wherein the viewing regions and the reinforcement regions are monolithic.

5. The reinforced sample support structure of claim 1 wherein the framing region comprises a material selected from the group consisting of monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, and combinations thereof.

6. A method of making a reinforced sample support structure, the sample support structure comprising (a) an array comprising more than one viewing region, wherein the viewing regions are supported by and divided by reinforcement regions and (b) a framing region surrounding the array, wherein the reinforcement regions and the viewing regions consist of the same material, said method comprising the following steps:
providing a substrate having a first surface and a second surface;
depositing a first support layer on the first surface of the substrate;
depositing a second support layer on the second surface of the substrate;
removing a portion of the first support layer to expose the substrate;
removing a portion of the substrate to yield the framing region;
thinning at least one region of the second support layer to provide the array comprising viewing regions supported by and divided by reinforcement regions, the reinforcement regions are thicker than the viewing regions, and wherein the reinforcement regions are positioned above the viewing regions and the framing region is positioned below the viewing regions,
wherein the framing region runs substantially along an outer edge of the reinforced sample support structure.

7. The method of claim 6 wherein the substrate comprises a material selected from the group consisting of monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, and combinations thereof.

8. The method of claim 6 wherein the substrate has a thickness ranging from about 2 to about 1000 µm.

9. The method of claim 6 wherein the first support layer comprises a material selected from the group consisting of monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, and combinations thereof.

10. The method of claim 6 wherein the second support layer has a thickness ranging from about 1 to about 1000 nm, which corresponds to the thickness of the reinforcement regions, and wherein the thickness of the viewing regions is less than the thickness of the reinforcement regions.

11. The method of claim 6 wherein the second support layer consists of a material selected from the group consisting of monocrystalline silicon, polycrystalline silicon, amorphous silicon, alumina, quartz, fused silica, boron nitride, silicon carbide, metals, ceramics, silicon nitride, aluminum nitride, gallium nitride, graphene, graphite, aluminum, titanium, copper, tungsten, diamond, aluminum oxide, conducting oxides, and combinations thereof.

12. The method of claim 6, wherein the second support layer consists of silicon nitride.

13. The method of claim 6, wherein the thinning is done by etching the second support layer.

14. The reinforced sample support structure of claim 1, wherein the reinforcement regions frame rectangular, circular, elliptical, or polygonal viewing regions.

15. The reinforced sample support structure of claim 1, wherein the imaging occurs through the viewing regions.

16. The reinforced sample support structure of claim 1, wherein the reinforcement regions frame the viewing regions.

17. The reinforced sample support structure of claim 1, wherein the thickness of the framing region is in a range from about 100 μm to about 750 μm, the thickness of the reinforcement regions is in a range from about 25 nm to 1000 nm, and the thickness of the viewing regions is less than the thickness of the reinforcement regions.

* * * * *